United States Patent
Tanaka et al.

(10) Patent No.: US 10,004,571 B2
(45) Date of Patent: Jun. 26, 2018

(54) CHUCK MECHANISM FOR DENTAL HANDPIECE AND DENTAL HANDPIECE USING THE MECHANISM

(75) Inventors: Hitoshi Tanaka, Kyoto (JP); Hiroyuki Ono, Kyoto (JP); Shozo Nakayama, Kyoto (JP)

(73) Assignee: J. MORITA MFG. CORP., Kyoto (JP)

(*) Notice: Subject to any disclaimer, the term of this patent is extended or adjusted under 35 U.S.C. 154(b) by 0 days. days.

(21) Appl. No.: 13/353,139

(22) Filed: Jan. 18, 2012

(65) Prior Publication Data

US 2012/0189979 A1    Jul. 26, 2012

(30) Foreign Application Priority Data

Jan. 25, 2011 (JP) ................................. 2011-012914
Jun. 29, 2011 (JP) ................................. 2011-144326

(51) Int. Cl.
    *A61C 1/14*    (2006.01)
(52) U.S. Cl.
    CPC .............. *A61C 1/141* (2013.01); *A61C 1/142* (2013.01); *A61C 1/144* (2013.01)
(58) Field of Classification Search
    CPC ............ A61C 1/14–1/144; A61C 1/145–1/148
    USPC ........ 279/23.1, 46.1, 46.2, 89; 433/127, 128
    See application file for complete search history.

(56) References Cited

U.S. PATENT DOCUMENTS

| 4,014,099 | A | * | 3/1977 | Bailey ........................... 433/128 |
| 4,370,132 | A | * | 1/1983 | Wohlgemuth ................. 433/128 |
| 5,924,865 | A | * | 7/1999 | Quinn ..................... A61C 1/144 |
| | | | | 433/127 |
| 7,645,138 | B2 | * | 1/2010 | Boinot .......................... 433/128 |
| 8,075,311 | B2 | * | 12/2011 | Pernot ........................... 433/128 |

FOREIGN PATENT DOCUMENTS

| JP | H04-090752 A | 3/1992 |
| JP | 2006-346452 A | 12/2006 |

* cited by examiner

*Primary Examiner* — Edward Moran
(74) *Attorney, Agent, or Firm* — Capitol City TechLaw

(57) ABSTRACT

A chuck mechanism for a dental handpiece holds a columnar rotary tool for dental care rotatably with an annular rotor of the dental handpiece. The columnar rotor tool is concentrically detachable to the annular rotor which is rotatably attached to a head part of the dental handpiece. The chuck mechanism has an annular chucking member with a cylindrical base part into which the annular rotor is integrally fitted and an elastic chucking piece having a chucking pawl for engaging with a locking groove formed at a base end of the rotary tool. The chuck mechanism enables the rotary tool to be easily removed from the annular rotor by elastically deforming the elastic chucking piece against elastic force of the elastic chucking piece to disengage the chucking pawl from the locking groove.

9 Claims, 14 Drawing Sheets

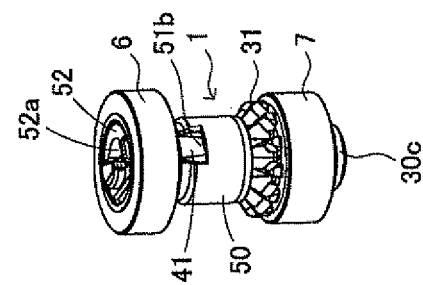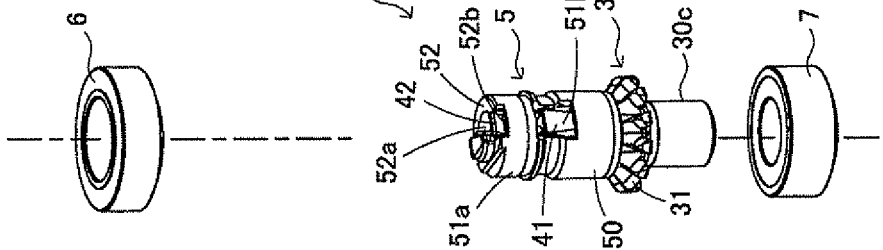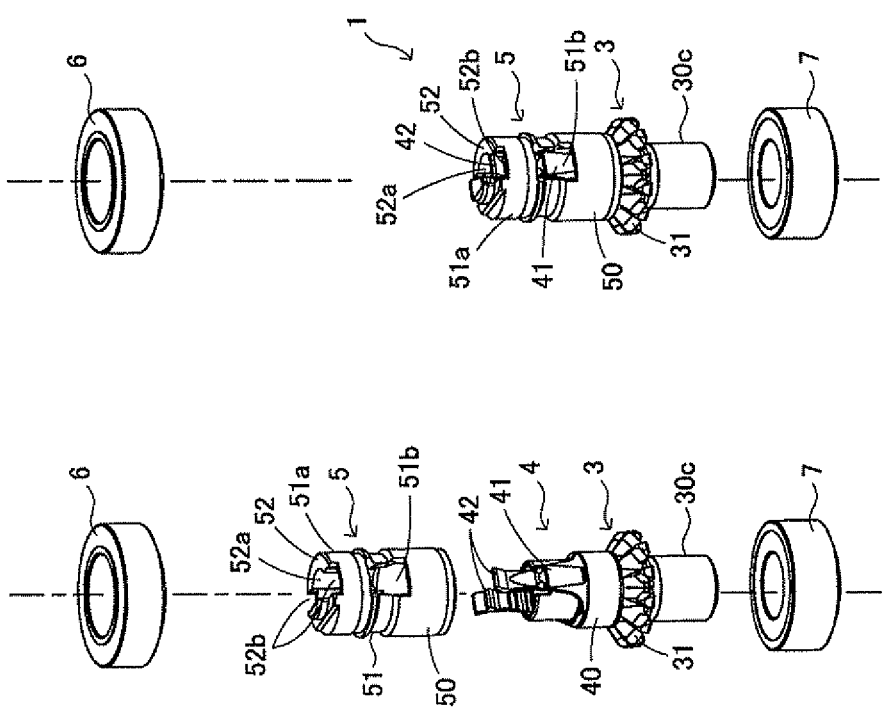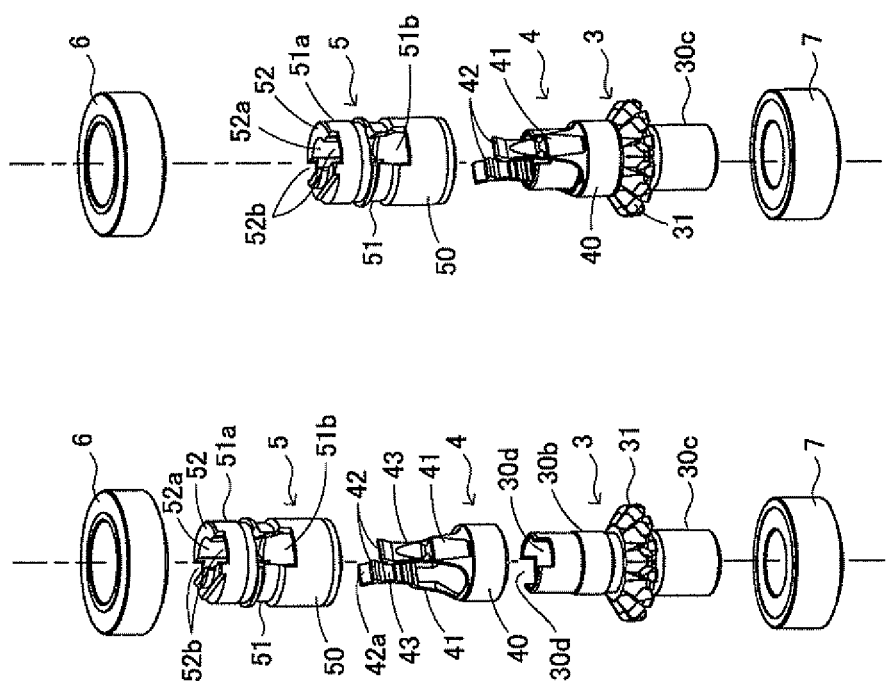

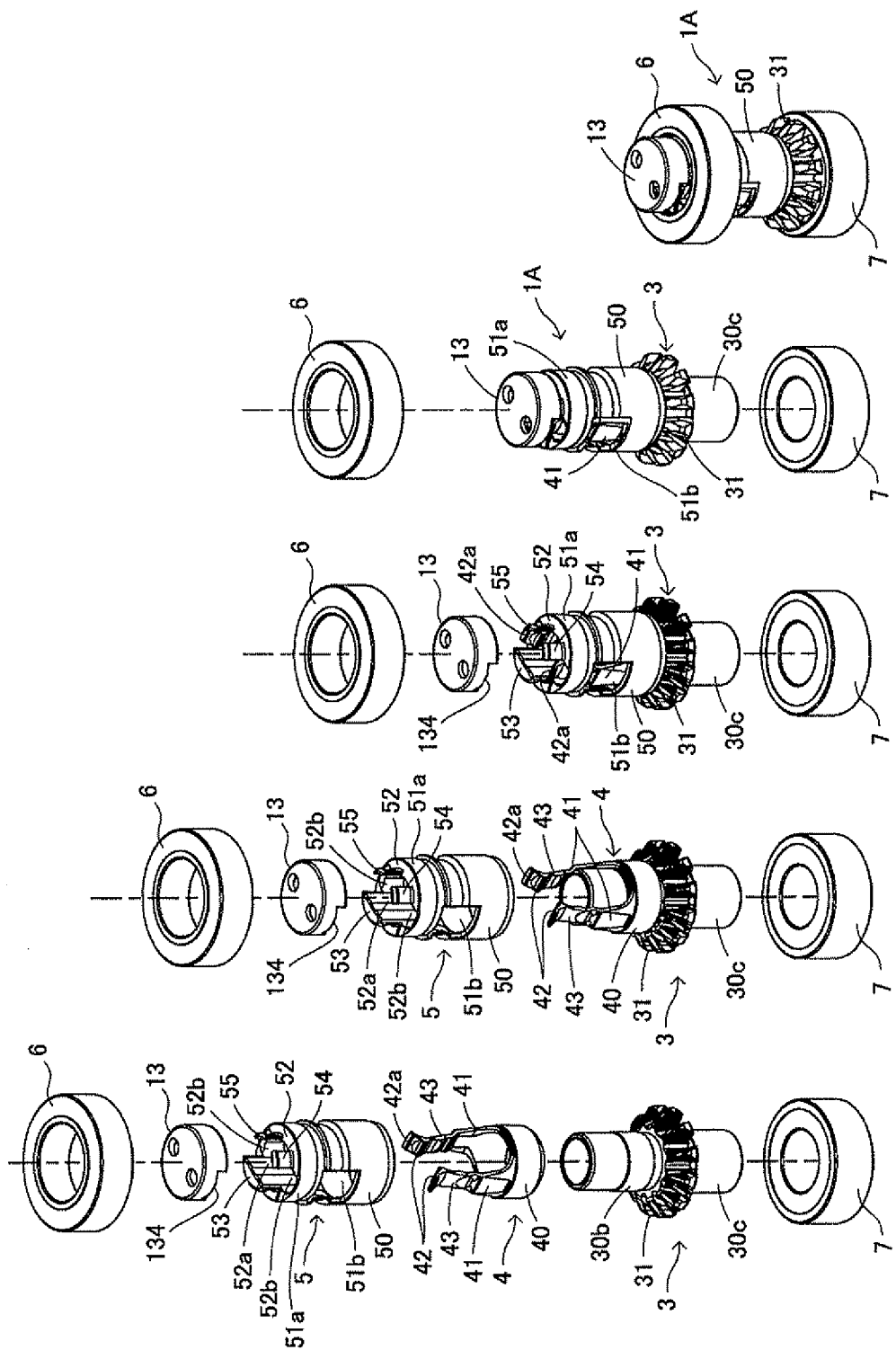

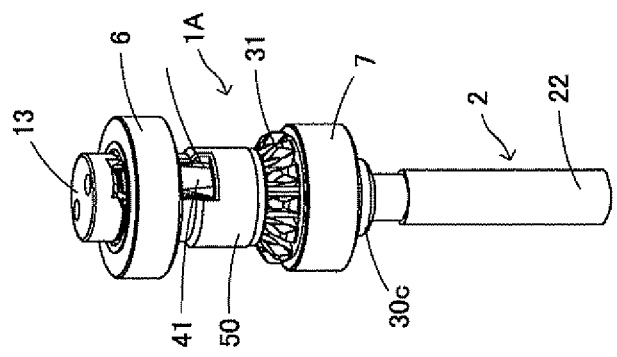
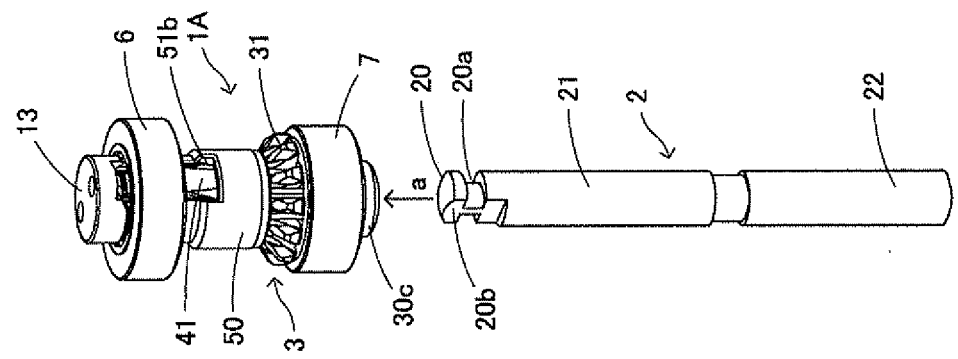

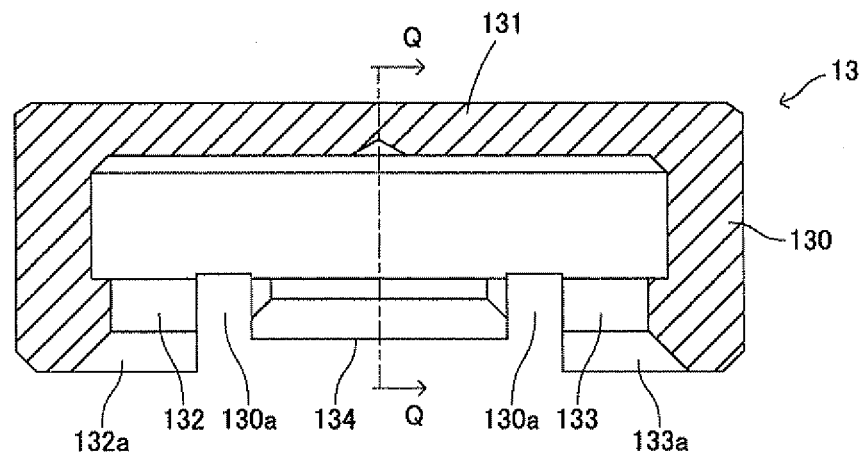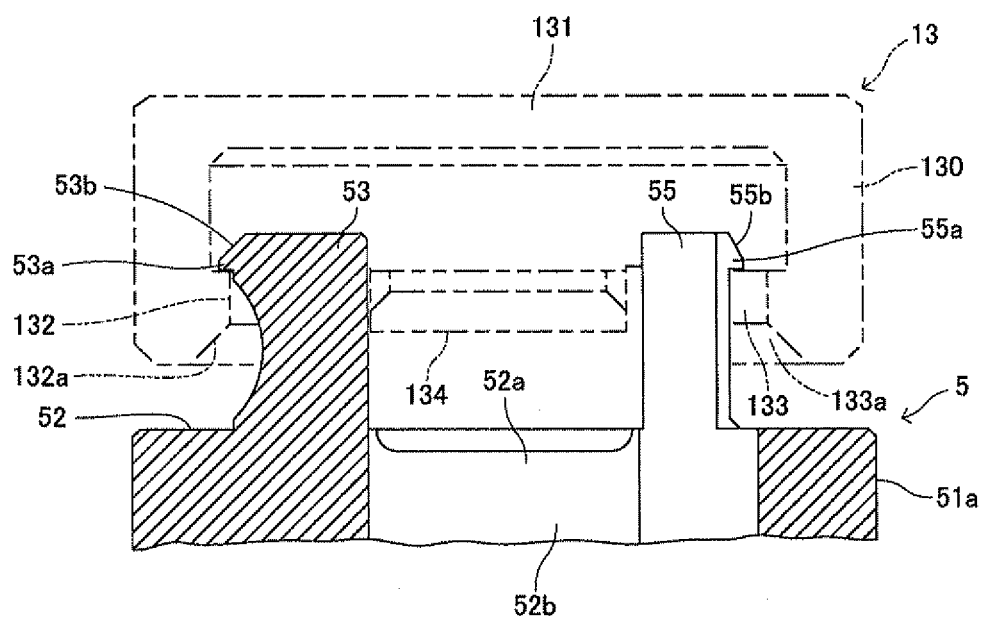
Fig.10

US 10,004,571 B2

CHUCK MECHANISM FOR DENTAL HANDPIECE AND DENTAL HANDPIECE USING THE MECHANISM

CROSS REFERENCE TO RELATED APPLICATIONS

This application claims the benefit of priority under 35 USC 119 of Japanese application no. 2011-012914, filed on Jan. 25, 2011, and Japanese application no. 2011-144326, filed on Jun. 29, 2011.

BACKGROUND OF THE INVENTION

Technical Field

The present invention relates to a chuck mechanism for detachably holding a rotary tool at a head part of a dental handpiece, specifically a micro-motor hand-held piece and further to a dental handpiece using the chuck mechanism.

Background Art

A dental micro-motor hand-held piece is designed such that a columnar rotary tool for cutting teeth (called contra-bar or latch bar) is detachably attached on a head part and axially rotates by rotary drive force of a micro-motor (rotary drive portion) embedded in the hand-held piece body. Several kinds of rotary tools are prepared and a suitable one is selected from them by an operator depending on the state of affected region and is used by attaching it on the head part. When the tip part (cutting operation part) of the rotary tool becomes worn, the tool is exchanged to a new one. Therefore, the rotary tool is designed so as to be easily attached or detached by a chuck mechanism incorporated into the head part. Such a chuck mechanism for a dental handpiece and a chuck device are disclosed in Patent Literatures 1 and 2, for example.

Patent Literature 1 discloses a chuck device for holding a contra-bar by locking a lock member to a locking groove formed at the upper end side (opposite to a cutting operation part, namely a base end part) of the contra-bar, the lock member being provided on the upper part (at the base end part side) of a bar tube (rotor) which receives and fixes the contra-bar and being capable of elastically reaming on a surface area orthogonal to the axial center of the bar tube. In the prior art (FIG. 11, FIG. 12) shown in Patent Literature 1, the chuck device is positioned on an inner diameter side of an upper bearing rotatably holding the bar tube. In the embodiment, it is pointed out as a problem that elastic function of the lock member cannot be adequately exerted even when the lock member is designed to be able to elastically ream (enlarge) in a limited space. Therefore, Patent Literature 1 proposes a chuck device as a new invention in which a lock member having similar function (of which structure is different) is positioned on the upper part of the upper bearing where a relatively larger movable space can be obtained for elastically reaming the lock member on a surface area orthogonal to the axial center of the bar tube.

Patent Literature 2 discloses a dental handpiece in which a manual button constituting a chuck release means is operated by pressing against the elastic force of a spring, the lower surface of the manual button abuts a ball provided on an upper surface of a pusher, and a chuck mechanism is released via the pusher by such abutting pressure.

PTL 1: JP-H04-90752-A
PTL 2: JP-2006-346452-A

The chuck device disclosed in PTL 1 as a new invention adequately exerts elastic function of the lock member; however, the head part becomes bulky in the axial center direction of the bar tube because the chuck device is positioned on the upper part of the upper bearing, so that such a device may not be suitable for a dental handpiece which is used to be inserted into narrow oral cavity.

FIG. 14a, FIG. 14b, and FIG. 14c diagrammatically show one embodiment of a chuck mechanism in practical use. FIG. 14a is a sectional view of the chuck mechanism shown with a rotary tool held with the chuck mechanism. FIG. 14b is a perspective view of a chucking member constituting the chuck mechanism. FIG. 14c is a left side view of FIG. 14a. The chuck mechanism 100 has a chucking member 101 shown in FIG. 14b. The chucking member 101 comprises a cylindrical base part 101a externally fitted to a shank part 102a of a columnar rotary tool 102 and a pair of elastic chucking pieces 101b in the shape of tongue having a chucking pawl 101c which axially extends from the cylindrical base part 101a and is elastically locked to a locking groove 102c formed at a base end part 102b of the rotary tool 102. A D-cut part 102d is further formed at the base end part 102b of the rotary tool 102 (refer to FIG. 14c). The tip part extending from the shank part 102a of the rotary tool 102 (opposite to the base end part 102b) is a cutting operation part 102e which projects from a head part, not shown, and is used for cutting teeth. A rotor 103 is externally fitted to the shank part 102a of the rotary tool 102. The rotor 103 has a tool guide tube part 103a externally fitted to the shank part 102a, a connection tube part 103b which is connected to the tool guide tube part 103a and is externally fitted to and integrated with the cylindrical base part 101a of the chucking member 101, and a driven-transmitted gear portion 103c which is formed on the outer circumference of the tool guide tube 103a.

In addition, a tubular rotor outer member 104 is externally fitted to and integrated with the connection tube part 103b of the rotor 103 and has a receiving part 104a formed corresponding to the shape of the base end part 102b having the D-cut part 102d of the rotary tool 102. When the base end part 102b is received in the receiving part 104a and they are engaged, mutual rotation of the rotor outer member 104 and the rotary tool 102 is made impossible. Namely, the rotor for axially rotating the rotary tool 102 is substantially constituted by the rotor 103 and the rotor outer member 104. Bearings 105, 106 are fitted and attached on the outer circumference of the tool guide tube part 103a of the rotor 102 and on the outer circumference of the base end part of the rotor outer member 104, respectively. The rotor outer member 104, the rotor 103, the chucking member 101, and the rotary tool 102 are integrally held to the head part, not shown, in an axially rotatable manner via the bearings 105, 106. A tapered cam-follower surface 101d which reams in the centrifugal direction is formed on the centrifugal side of the chucking pawl 101c of the chucking member 101. When a push button, not shown, attached on the head part, is operated along the axial direction to the cam-follower surface 101d, the elastic chucking piece 101b is pushed and enlarged against the elastic force and the chucking pawl 101c is made disengageable from the locking groove 102c. When the chucking pawl 101c is disengaged from the locking groove 102c, the rotary tool 102 can be removed from the rotor 103.

In the chuck mechanism 100 of the rotary tool 102 constituted as in FIG. 14, the elastic chucking piece 101b of the chucking member 101 extends in the axial direction from the cylindrical base part 101a, so that the elastic deformation is not limited and locking and disengaging functions of the chucking pawl 101c to and from the locking groove 102c can be adequately exerted. However, the cylindrical base part 101a of the chucking member 101 is integrated in the inner circumference of the rotor 102, so that there is a problem that circumscribed length L1 along the axial direction of the tool guide tube part 103a to the shank part 102a of the rotary tool 102 is not adequately secured. The inner diameter of the tool guide tube part 103a is made slightly larger than the outer diameter of the shank part 102a considering the insertion ability of the rotary tool 102. When the circumscribed length L1 is not largely secured, the rotary tool 102 and the rotor 103 cause axial runout, although the rotary force of the rotor 103 is directly transmitted to the rotary tool 102 in the circumscribed length L1. If the hand-held piece is used for a long time when they cause axial runout, cut powder caused by the cutting operation part 102e is accumulated and solidified between the shank 102a and the tool guide tube part 103a, as a result the rotary tool 102 is not able to be removed.

SUMMARY OP THE INVENTION

The object of the present invention is to provide a chuck mechanism for a dental handpiece which can adequately exert elastic chuck function and can reduce axial runout (deflection of axial center) caused by the rotor at a holding part of the rotary tool and further to provide a dental handpiece using the mechanism.

According to a chuck mechanism for a dental handpiece for rotatably holding a columnar rotary tool for dental care with an annular rotor of the dental handpiece, the columnar rotor tool being concentrically detachable to the annular rotor which is rotatably attached to a head part of the dental handpiece of the present invention, the chuck mechanism comprises an annular chucking member, and the annular chucking member comprises a cylindrical base part into which the annular rotor is integrally fitted and an elastic chucking piece having a chucking pawl for elastically engaging with a locking groove at a base end of the rotary tool which is formed extending in its axial direction from the cylindrical base part. The rotary tool is removed from the annular rotor by deforming the elastic chucking piece against elastic force of the elastic chucking piece to disengage the chucking pawl from the locking groove.

According to the chuck mechanism for a dental handpiece, in the sate that the rotary tool is fitted into the annular rotor, the rotary tool can be fitted into the annular rotor in a manner that most of the inner diametrical part of the annular rotor contacts the rotary tool along the outer circumference of a shank part of the rotary tool, and the annular chucking member can be externally fitted to the annular rotor in a manner that the outer circumference other than the chucking pawl and its vicinity of the chucking member contacts the annular rotor.

In addition, the elastic chucking piece can be provided symmetrically along its axis as a pair, and the elastic chucking pieces can be elastically deformable in radial direction of the rotary tool relative to an axial center of the rotary tool.

According to the present invention, the chuck mechanism for a dental handpiece can further comprise a tubular rotor outer member which is externally fitted to the cylindrical base part of the chucking member, and the rotary tool can be engaged with the rotor outer member at its base part in a manner that the rotary tool and the rotor outer member are not rotatable each other. In such an embodiment, the tubular rotor outer member can have a bearing at its radial outward part with which the rotor is rotatably fitted to the head part of the dental handpiece. In addition, the bearing can be fitted to a corresponding region where the chucking pawl and the locking groove are engaged.

Furthermore, when the above-mentioned rotor outer member is provided, to a region of the rotor outer member where the rotary tool is engaged in the sate that they are not rotatable each other, a working body having a cap like shape movable along its axis can be fitted in a manner that the working body is non-disengageable and they are not rotatable each other, and the working body can have an operation part for letting the elastic chucking piece deform against elastic force of the elastic chucking piece accompanying the movement of the working body. In such an embodiment, the working body can have a short cylindrical part and a flat canopy part for closing one end of the short cylindrical part, and the cylindrical part can be provided with the operation part and a locking part for attaching the working body to the rotor outer member movably in its axial direction and non-disengageable.

According to the present invention, the dental handpiece comprises the hand-held piece body, the head part connected to a front end of the hand-held piece body, a rotary drive portion built in the hand-held piece body, a rotation transmitting portion for transmitting rotary force from the rotary drive portion, the chuck mechanism as provided at the head part for the dental handpiece as mentioned above and a chuck release means for the chuck mechanism. The rotary tool for dental care held with the chucking mechanism is constructed such that it rotates together with the rotor around its axis by rotary force transmitted from the rotation transmitting portion.

According to the present invention, the columnar rotary tool is axially rotatably held at the head part connected to the hand-held piece body by the chuck mechanism of the present invention. The rotary drive portion is embedded in the hand-held piece body, rotary power from the rotary drive portion is transmitted by the rotation transmitting portion, the rotary power is obtained from the rotation transmitting portion, then the rotary tool axially rotates with the rotor. The chucking pawl of the chucking member constituting the chuck mechanism is elastically locked in the locking groove formed at the base end part of the rotary tool which is inserted into the rotor, so that the rotary tool is prevented from being removed. The chucking pawl is provided at the elastic chucking piece axially extending from the cylindrical base part externally fitted and integrated to the rotor, the elastic chucking piece is elastically deformed against the elastic force by operating the chuck release means, and the chucking pawl can be disengaged from the locking groove. Thereby the rotary tool can be removed from the rotor, so that the elastic deformation of the elastic chucking piece is not limited in space and elastic chucking function can be adequately exerted. In addition, the cylindrical base part of the chucking member is externally fitted and integrated to the rotor, so that the circumscribed length of the rotor along the axial direction to the rotary tool can be widely secured, thereby reducing axial runout of the rotor and the rotary tool. Therefore, abrasion caused by friction of the rotor and the rotary tool is reduced, and it hardly happens that abrasion powder is accumulated and solidified between the rotor and the rotary tool and the rotary tool cannot be removed when the hand-held piece is used for a long time. In addition, when the axial runout of the rotary tool becomes small, pain caused by intermittent contact between a tooth and the rotary tool in the process of tooth cutting cut can be reduced, thereby relieving a patient.

In the present invention, when most of the inner circumference of the rotor is circumscribed with the shank part of the rotary tool while the rotary tool is inserted into the rotor, the circumscribed length of the rotor to the shank part can be widely secured, thereby further effectively reducing the axial runout. When the portion other than the chucking pawl and its vicinity of the chucking member is externally fitted to the rotor, the circumscribed length of the rotor to the shank part can also be widely secured.

In the present invention, when a pair of the elastic chucking pieces are axisymmetrically provided and are elastically deformable in the radial direction to the axial center of the rotary tool, a pair of the chucking pawls can be locked in the locking groove so as to sandwich the base end part of the rotary tool. Therefore, the non-removable state of the rotary tool can be stably kept by such locking. In addition, the elastic chucking pieces are provided axisymmetrically, so that the force applied on the rotary tool along the radial direction can be uniform, thereby further reducing the axial runout.

In the present invention, the tubular rotor outer member which is externally fitted and integrated to the cylindrical base part of the chucking member can be further provided and the base part of the rotary tool can be engaged with the rotor outer member so as not to be rotatable each other. In this case, the chucking member and the rotor are integrated and the chucking member and the rotor outer member are also integrated, thereby the rotor and the rotor outer member become integrated. In addition, the rotary tool is engaged with the rotor outer member so as not to be rotatable each other, thereby the rotary force of the rotor is transmitted to the rotary tool via the chucking member and the rotor outer member. In this case, when the bearing for rotatably attaching the rotor to the head part is fitted and attached at the outer circumference of the rotor outer member, space required for the chuck mechanism in the head part can be reduced. In addition, when a portion of the rotor outer member to which the bearing is fitted corresponds to a locking part of the chucking pawl of the chucking member and the locking groove of the rotary tool, the space can be further reduced, thereby reducing bulk of the head part in the axial direction and keeping suitability as a dental handpiece which is used to be inserted into narrow oral cavity.

When the rotor outer member is provided and the working body is attached to the rotor outer member as mentioned above, the chuck release means is operated on the working body, thereby elastically deforming the elastic chucking piece by the operation part against the elastic force. Namely, when the chuck release means is operated, the chucking pawl of the elastic chucking piece can be disengaged from the locking groove via the working body. Therefore, even when the chuck release means is operated by mistake while the rotary tool still rotates by inertia after rotation of the rotary tool is stopped, there is no fear of causing abrasion at the elastic chucking piece and the operation part by mutual rotation of the elastic chucking piece and the operation part because the working body and the rotary tool (rotor, chucking member and the rotor outer member) are integrally rotated. When the working body has the short cylindrical part and the flat canopy part closing one end of the cylindrical part and the cylindrical part is provided with the operation part and the locking part for attaching the working body to the rotor outer member in such a manner that the working body is movable in the axial direction and is non-disengageable, the rotary tool can be attached to or detached from the chuck mechanism while the chuck release means is operated on the flat canopy. Therefore, when the rotary tool is attached, the rotor outer member is fixed by abrasion resistance of the flat canopy and the chuck release means, thereby accurately engaging the rotary tool with the rotor outer member in a manner that they cannot rotate each other.

BRIEF DESCRIPTION OF THE SEVERAL VIEWS OF THE DRAWINGS

FIG. 1a is a sectional view showing the chuck mechanism together with the rotary tool held with the chuck mechanism, FIG. 1b is a perspective view of the chucking member constituting the chuck mechanism, FIG. 1c is a front view of the chucking member, and FIG. 1d is a side view of FIG. 1a.

FIG. 2a, FIG. 2b, FIG. 2c, and FIG. 2d are perspective views showing assembly procedures of the chuck mechanism of the embodiment.

FIG. 7a, FIG. 7b, FIG. 7c, FIG. 7d and FIG. 7e are perspective views showing assembly procedures of the chuck mechanism in another embodiment.

FIG. 8a and FIG. 8b are perspective views showing procedures when the rotary tool is further assembled to the chuck mechanism in the embodiment.

FIG. 10 is a sectional view taken along the arrow P-P in FIG. 9.

FIG. 14a is a sectional view showing the chuck mechanism together with the rotary tool held with the chuck mechanism, FIG. 14b is a perspective view of the chucking member constituting the chuck mechanism, and FIG. 14c is a side view of FIG. 14a.

DETAILED DESCRIPTION OF THE INVENTION

Figure 1A:
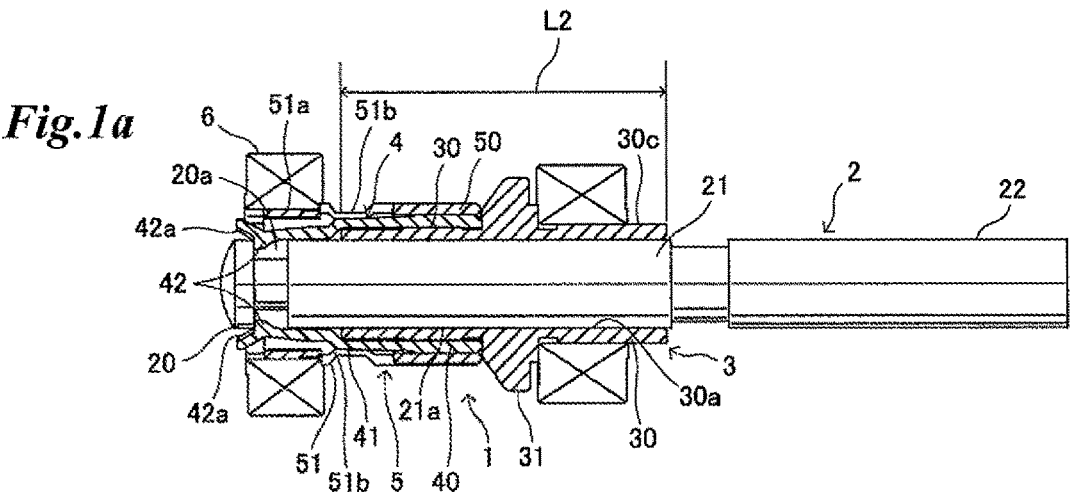
FIG. 1a, FIG. 1b, FIG. 1c, and FIG. 1d show one embodiment of the chuck mechanism of the present invention.
Figure 1B:
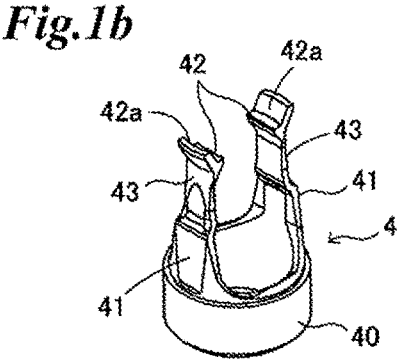
Figure 1C:
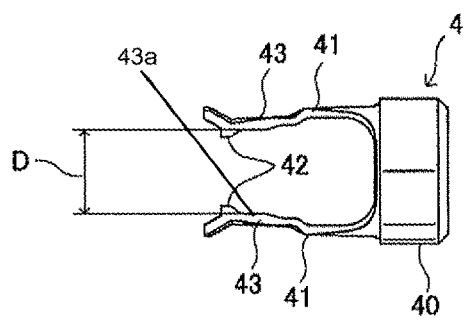

The embodiments of a chuck mechanism for a dental handpiece and a dental handpiece using the mechanism according to the present invention are explained based on the drawings. In the chuck mechanism 1 shown in FIG. 1a, a tubular rotor 3 is externally fitted to a shank part 21 of a rotary tool (a contra-bar or a latch bar) 2. The rotor 3 has a tool guide tube part 30 to which the shank part 21 of the rotary tool 2 is inserted so as to be held along the entire length and an inner circumference 30a of the tool guide tube part 30 circumscribes with the shank part 21 of the rotary tool 2. The circumscribed length is represented as L2. The chuck mechanism 1 has a chucking member 4 as shown in FIG. 1b and FIG. 1c. The chucking member 4 has a cylindrical base part 40 which is externally fitted to and integrated with an outer circumference 30b of the tool guide tube part 30 on the side of a base end part 20 of the rotary tool 2 (called outer circumference on the base end side, hereinafter), the tool guide tube part 30 being externally fitted to the shank part 21 of the rotary tool 2. The chuck mechanism 4 also has a pair of elastic chucking pieces 41, 41 in the form of a tongue with a chucking pawl 42 which extends from the cylindrical base part 40 along the axial direction (in a direction of axial center of the rotary tool 2) and is elastically locked to an locking groove 20a formed at the base end part 20 of the rotary tool 2. The elastic chucking pieces 41, 41 are axisymmetrically provided and chucking pawls 42, 42 provided for them respectively are positioned so as to face each other.

Figure 1D:
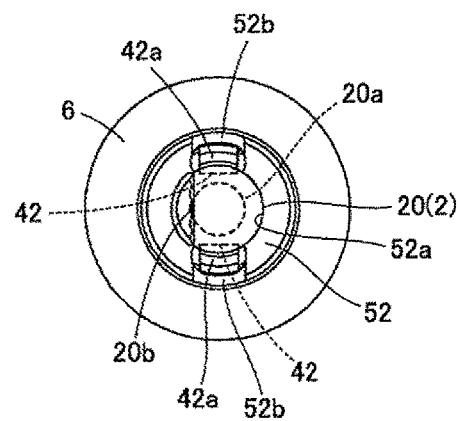

Sections extending from the middle of the elastic chucking pieces 41, 41 to the chucking pawls 42, 42 are defined as abutting parts 43, 43 which directly abut the shank part 21 of the rotor 3 and the inside distance D (refer to FIG. 1c) between the abutting parts 43, 43 is designed to be slightly smaller than the outer diameter of the shank part 21. Therefore, when the rotary tool 2 is inserted into the rotor 3 and the chucking member 4, the abutting parts 43, 43 are elastically deformed to be pushed and enlarged by the shank part 21 and come to elastically abut an outer circumference 21a of the shank part 21 by the restoration resilience. The distance between the facing chucking pawls 42, 42 is designed to be smaller than the inside distance D and elastic locking of the chucking pawls 42, 42 to the locking groove 20a is stably kept by elastic abutment of the abutting parts 43, 43 to the outer circumference 21a of the shank part 21. When the abutting parts 43, 43 elastically abut so as to hold the shank part 21, the rotary tool 2 is prevented from vibrating and abrasion of the shank part 21 of the rotary tool 2 and the inner circumference 30a of the tool guide tube part 30 is reduced. Tapered cam-follower surfaces 42a, 42a reamed in the centrifugal direction are formed so as to face each other at the back of the chucking pawls 42, 42 in the centrifugal direction. The cylindrical base part 40 is, externally fitted to and integrated with the outer circumference 30b on the side of the base end part by means of mutual press-fit, spot welding, or a combination of press-fit and spot welding. A D-cut part 20b is further provided for the base end part 20 of the rotary tool 2 (refer to FIG. 1d and FIG. 3a). A tip part from the shank part 21 (opposite to the base end part 20) of the rotary tool 2 projects from a head part 9 of a dental handpiece 8 shown in FIG. 4 and FIG. 5 and is formed as a cutting operation part 22 provided for cutting teeth. The rotor 3 has a driven-transmitted gear portion 31 at the outer circumference of the middle section in the length direction.

A tubular rotor outer member 5 is externally fitted to and integrated with the cylindrical base part 40 of the chucking member 4. The rotor outer member 5 has a base ring part 50 which is externally fitted to and integrated with the cylindrical base part 40 of the chucking member 4 by press-fit or spot welding as mentioned above and has a cylindrical part 51 concentrically connected to the base end 20 side of the rotary tool 2 from the base ring 50. A disc part 52 is formed at the base end of the cylindrical part 51 (opposite to the base ring part 50) referring to FIG. 1d, and the disc part 52 has a receiving part 52a formed corresponding to the shape of the base end part 20 of the rotary tool 2 having the D-cut part 20b. When the base end part 20 of the rotary tool 2 is received and engaged with the receiving part 52a, the rotor outer member 5 and the rotary tool 2 cannot rotate each other. Namely, the rotor 3, the chucking member 4 and the rotor outer member 5 substantially constitute a rotor for axially rotating the rotary tool 2.

Figure 4:
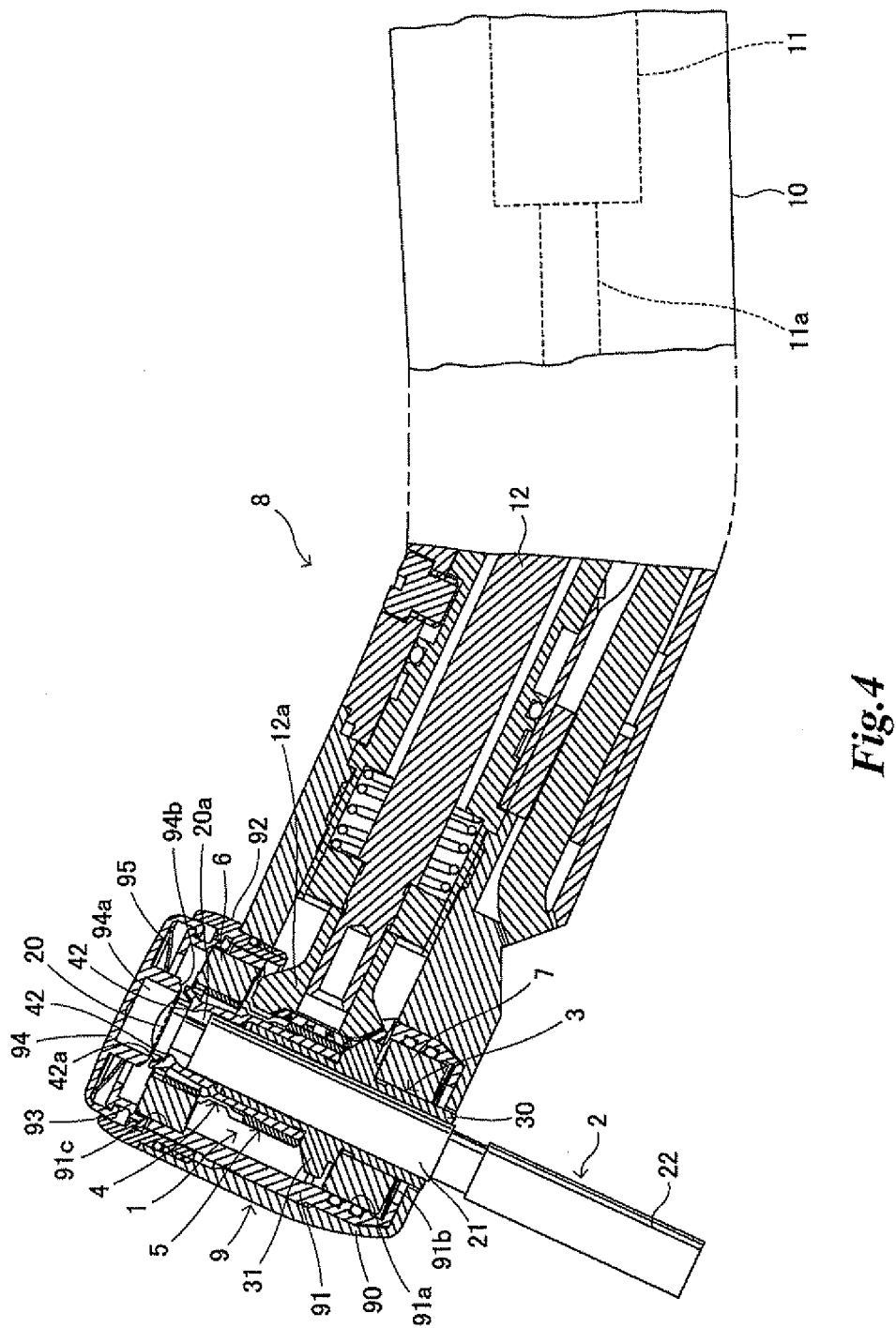
FIG. 4 is a partially broken sectional view of a substantial part of one embodiment of the dental handpiece having the chuck mechanism.
Figure 5:
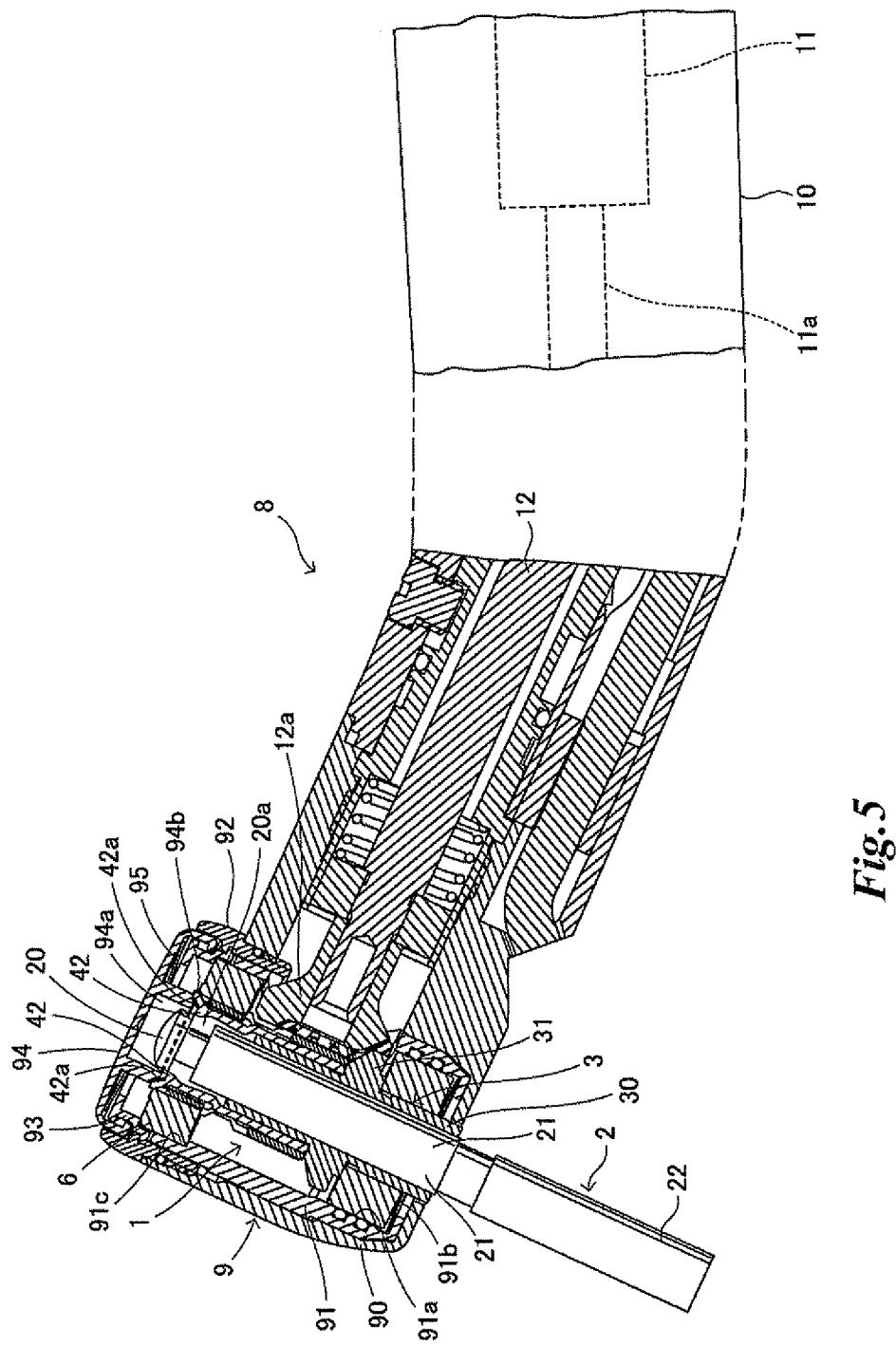
FIG. 5 is a similar view to FIG. 4 showing removing procedures of the rotary tool from the dental handpiece.

The cylindrical part 51 adjacent to the disc part 52 constitutes a tubular bearing holding part 51a and a base end side bearing 6 is fitted and attached at the outer circumference of the tubular bearing holding part 51a. Namely, a portion of the rotor outer member 5 to which the base end side bearing 6 is fitted is a portion corresponding to a locking part of the chucking pawls 42, 42 of the chucking member 4 and the locking groove 20a of the rotary tool 2. Therefore, bulk of the chuck mechanism in the axial direction is reduced. Pocket parts 52b, 52b in which the chucking pawls 42, 42 of the chucking member 4 can elastically fluctuate are provided so as to be radially broadened from the receiving part 52a. In addition, longitudinal grooves 51b, 51b in which the elastic chucking pieces 41, 41 can elastically fluctuate are formed along the axial direction on the tube wall of the cylindrical part 51. A tip side bearing 7 is fitted and attached to an outer circumference 30c extending from the driven-transmitted gear portion 31 of the tool guide tube part 30 of the rotor 3 (called outer circumference on the tip side). The rotor outer member 5, the chucking member 4, the rotor 3 and the rotary tool 2 are integrally and axially-rotatably held at the head part 9 of the dental handpiece 8 via the base end side bearing 6 and the tip side bearing 7 as shown in FIG. 4 and FIG. 5. Cutouts 30d, 30d are formed for receiving extended base parts of the elastic chucking pieces 41, 41 on the end of the base end side of the tool guide tube part 30.

Next, assembly procedures of the chuck mechanism 1 including the above-mentioned structure members are explained referring to FIG. 2. Each structure member is provided in a concentric manner each other as shown in FIG. 2a. Firstly, the cylindrical base part 40 of the chucking member 4 is fitted to the tool guide tube part 30 of the rotor 3 from its base end part, and the cylindrical base part 40 is externally fitted to and integrated with the outer circumference 30b on the base end side of the tool guide tube part 30 by press-fit and so on as shown in FIG. 2b Such external fitting and integration is done in such a manner that the elastic chucking pieces 41, 41 are aligned with the cutouts 30d, 30d. In addition, the base ring part 50 of the rotor outer member 5 is externally fitted to and integrated with the cylindrical base part 40 of the chucking member 4 by press-fit as mentioned above, as shown in FIG. 2c. Such external fitting and integration is done in such a manner that the elastic chucking pieces 41, 41 are aligned with the longitudinal grooves 51b, 51b and the chucking pawls 42, 42 are aligned with the pocket parts 52b, 52b. Accordingly, assembly of the chuck mechanism 1 is completed. Then, the base end side bearing 6 and the tip side bearing 7 are fitted to the tubular bearing holding part 51a of the rotor outer member 5 and the outer circumference 30c on the tip side of the rotor 3, respectively. The chuck mechanism 1 is assembled to a predetermined portion of the head part 9 of the dental handpiece 8 shown in FIG. 4 and FIG. 5.

Figure 3A:
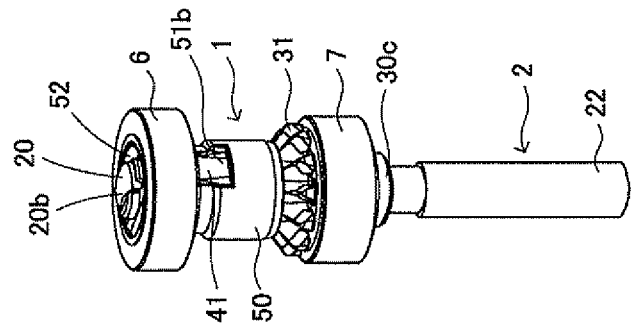
FIG. 3a and FIG. 3b are perspective views showing procedures when the rotary tool is further assembled to the chuck mechanism in the embodiment.
Figure 3B:
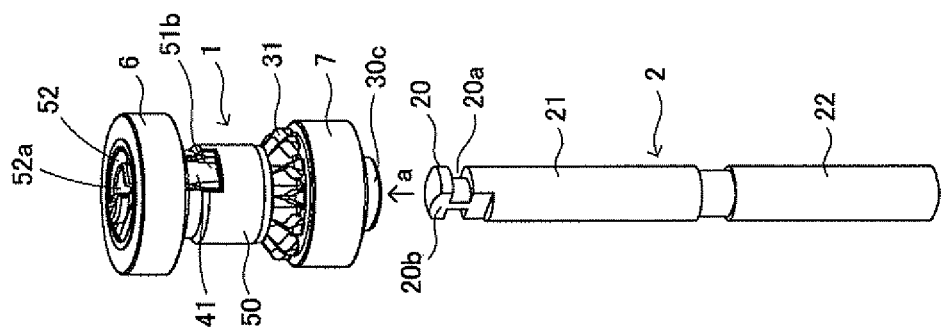

FIG. 3a and FIG. 3b show assembly procedures of the rotary tool 2 to the chuck mechanism 1 assembled to the head part 9. The head part 9 is not shown for convenience in FIG. 3. The base end part 20 of the rotary tool 2 is inserted into the tool guide tube part 30 of the rotor 3 from the opening at tip side as shown with the arrow "a" in FIG. 3a. The shank part 21 operates on the abutting parts 43, 43 of the chucking member 4 and deforms the elastic chucking pieces 41, 41 so as to be pushed and enlarged in the centrifugal direction, thereby the shank part 21 is inserted. When the base end part 20 reaches the lower surface of the disc part 52, the rotary tool 2 is manipulated to axially rotate and to be positioned in such a manner that the base end part 20 having the D-cut part 20b is aligned with the receiving part 52a. In such an aligned state, the rotary tool 2 is further pushed in the direction "a", the base end part 20 is engaged with the receiving part 52a and the rotary tool 2 and the rotor outer member 5 become unable to rotate each other. In addition, the elastic chucking pieces 41, 41 elastically restore and the chucking pawls 42, 42 are fitted in the locking groove 20a to be locked therein. The abutting parts (43) have inner main surfaces (43a) that abut the outer circumference of the shank part 21 in a radial direction so as to be elastically held.

The rotary tool 2 is actually assembled in such a manner that the elastic chucking pieces 41, 41 are pushed and enlarged in the centrifugal direction by means of chuck release means, which is explained referring to FIG. 4 and FIG. 5, and the rotary tool 2 is inserted in the direction "a".

FIG. 3b shows the rotary tool 2 is assembled to the chuck mechanism 1, in which the rotary tool 2 is prevented from being removed from the tool guide tube part 30 and the rotary tool 2, the rotor 3, the chucking member 4 and the rotor outer member 5 can be integrally held in an axially rotatable manner by means of the bearings 6, 7. Since the elastic chucking pieces 41, 41 always have elastic restoration resilience in the centripetal direction, the chucking pawls 42, 42 do not remove from the locking groove 20a, thereby keeping a stably locked state. The elastic chucking pieces 41, 41 are elastically enlarged in the centrifugal direction using a fulcrum point at an extended base of the cylindrical base part 40 of the elastic chucking pieces 41, 41 when the rotary tool 2 is inserted, so that elastic function can be accurately exerted in a small space. In addition, the longitudinal grooves 51b, 51b are formed at a portion facing the elastic chucking pieces 41, 41 of the cylindrical part 51 of the rotor outer member 5 in this embodiment, thereby facilitating such elastic enlarging operation. The chucking pawls 42, 42 are elastically enlarged in the centrifugal direction when the rotary tool 2 is inserted, and such enlarging operation can also be facilitated because the pocket parts 52b, 52b are provided for the disc part 2.

FIG. 4 and FIG. 5 show one embodiment of a dental handpiece incorporating the chuck mechanism 1. The dental handpiece 8 in the figures is a micro-motor hand-held piece of contra-angle type in which the head part 9 is detachably connected to a hand-held piece body 10 as a grip part. The detachable connection mechanism is the same as the conventional one, so it is not shown in the figures and its explanation is omitted here. A micro-motor (rotary drive portion) 11 is embedded in the hand-held piece body 10, and an output shaft 11a is coupled to a drive-transmission shaft 12 in the head part 9 via a coupling part (not shown) provided therebetween. A drive-transmission gear part 12a which is engaged with the driven-transmitted gear portion 31 of the rotor 3 is provided at the tip end of the drive-transmission shaft 12. Both gear parts 31, 12a constitute a bevel gear and the rotary power is transmitted so as to rotate the rotor 3 around the axial center orthogonal to the axial center of the drive-transmission shaft 12. The drive-transmission shaft 12, the drive-transmission gear part 12a and the driven-transmitted gear portion 31 constitute a rotation transmission portion.

A housing 90 for containing the chuck mechanism 1 is provided at the tip part of the head part 9, the upper end of the housing 90 (on the side of the base end 20 of the rotary tool 2) is open, and a cylindrical distance piece 91 is provided in the housing 90 from the opening. The chuck mechanism 1 is contained in the tubular distance piece 91 in a fitted state. The bottom side of the distance piece 91 is formed as a tip side bearing holding part 91a for holding the tip side bearing 7 and the tip side bearing 7 side is held with the tip side bearing holding part 91a in an elastically energized state in upward direction (on the opening side) by a disc spring 91b. The upper end of the distance piece 91 is formed as a base end side bearing holding part 91c and holds the base end side bearing 6. A support ring 92 is screwed at the opening of the housing 90 together with a cap ring 93 for pushing the base end side bearing 6 to the base end side bearing holding part 91c. The pushing force of the cap ring 93 operates on the tip side bearing 7 via the driven-transmitted gear portion 31 of the rotor 3, and compresses the disc spring 91b, thereby the chuck mechanism 1 can be stably held to the distance piece 91 by the compressed restoration resilience. In addition, a push button 94 is attached to the cap ring 93 in such a manner that the button 94 can be latched movably along the axial center direction of the rotary tool 2. A disc spring 95 in the shape of a waved washer is elastically fitted between the push button 94 and the cap ring 93 and the push button 94 is always elastically energized in upward direction by the disc spring 95. The push button 94 and the support ring 92 substantially constitute a cap for closing the opening of the housing 90. A cylindrical projection 94a is formed as a tapered operation surface 94b (hereinafter called cam surface) on the lower surface of the pushbutton 94 in such a manner that the projecting end is gradually reduced into the tip part. The cam surface 94b is positioned at a portion facing the cam-follower surfaces 42a, 42a of the elastic chucking pieces 41, 41. The push button 94 including the cam surface 94b and the disc spring 95 constitute a chuck release means of a rotary tool. The portion of the rotor outer member 5 where the base end side bearing 6 is fitted and attached is positioned on the outer circumference of a portion where the chucking pawls 42, 42 are locked in the locking groove 20a, so that only the cap ring 93 and the push button 94 are provided on the upper part of the base end part 20 of the rotary tool 2 and the head part 9 does not become bulky in the axial direction.

As mentioned above, the push button 94 can be pressed against the elastic force of the disc spring 95 relative to the chuck mechanism 1 incorporated in the head part 9, and the elastic chucking pieces 41, 41 can be elastically reamed in the centrifugal direction. In such a manner, the rotary tool 2 is inserted into the tool guide tube part 30 positioned at the lower end of the head part 9 according to the procedures shown in FIG. 3a and FIG. 3b and is rotatably held in the head part 9 together with the rotor 3, the chucking member 4 and the rotor outer member 5. In case of using the dental handpiece 8, when the micro-motor 11 is turned on, the rotary power is transmitted from the output shaft 11a to the drive-transmission shaft 12. The rotary power is transmitted to the driven-transmitted gear portion 31 of the rotor 3 from the drive-transmission gear part 12a, converted to the rotary movement in direction orthogonal to the rotary axis center, so that the rotary tool 2 axially rotates. The cutting operation part 22 of the rotary tool 2 is assigned to an objective affected region of a tooth to be treated and cutting treatment is executed on the region by rotation. The cutting operation part 22 the surface of which is fixed with hard abrading agent such as diamond powder is preferably used.

FIG. 5 shows chuck release of the rotary tool 2 from the chuck mechanism 1, namely removal procedures of the rotary tool 2 from the rotor 3. When the push button 94 is pressed against the elastic force of the disc spring 95 along the axial center direction of the rotary tool 2 while the rotor 3 stops rotation, the cam surface 94b formed on the projecting end of the cylindrical projection 94a abuts the cam-follower surfaces 42a, 42a of the elastic chucking pieces 41, 41, the component force of the pushing force operates by both inclined surfaces to push apart the elastic chucking pieces 41, 41 into the centrifugal direction. When the chucking pawls 42, 42 are disengaged from the locking groove 20a and the cutting operation part 22 is pulled with finger, the rotary tool 2 can be removed from the rotor 3.

Figure 6A:
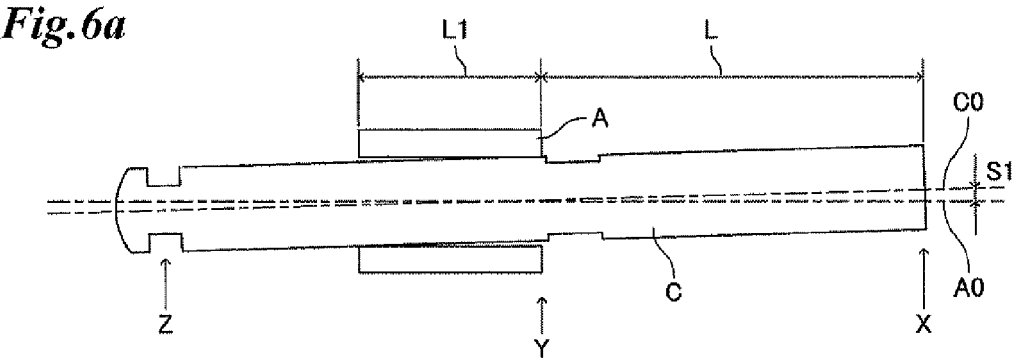
FIG. 6a and FIG. 6b show explanatory views showing operation principle of the chuck mechanism and show embodiments in which the circumscribed lengths of the rotor to the rotary tool are different.
Figure 6B:
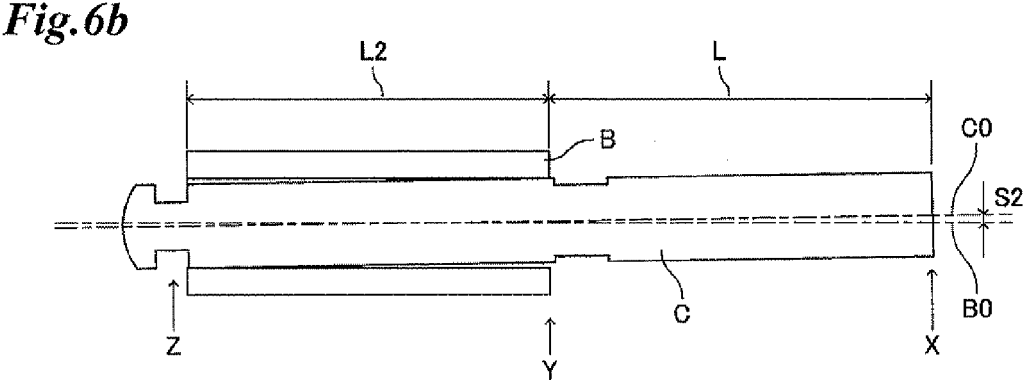

Next, operation principle depending on the difference of the circumscribed length of the rotor relative to the rotary tool is explained referring to FIG. 6a and FIG. 6b. The rotary tool is represented with "C", a rotor having short circumscribed length of the tool guide tube part relative to the rotary tool is represented with "A", and a rotor having long circumscribed length thereof is represented with "B" for convenience. FIG. 6a shows the circumscribed length is short as in prior art and FIG. 6b shows the circumscribed length is long as in the present invention. Circumscribed lengths are represented with L1 and L2, and the length from the tip end "X" of the rotary tool to the tip side end "Y" of the rotor is represented with "L". When the force applied to the tip end "X" of the rotary tool "C" by rotary cutting operation is defined as F0, the forces F0 in FIG. 6a and FIG. 6b are considered to be same. The force F1a applied on the tip side end "Y" of the rotor "A" in FIG. 6a is represented with the formula F1a=F0 (L+L1)/L1. The force F1b applied on the tip side end "Y" of the rotor B in FIG. 6b is represented with the formula F1b=F0 (L+L2)/L2. Because L2 is larger than L1, F1b becomes smaller than F1a.

In case that F0=5N, L=10.6 mm, L1=5.1 mm, L2=10.1 mm, the following results are gained.

$$F1a=F0(L+L1)/L1=5(10.6+5.1)/5.1=15.4N$$

$$F1b=F0(L+L2)/L2=5(10.6+10.1)/10.1=10.2N$$

F1b becomes smaller than F1a by 5N. Therefore, it is understood that the force applied on the inner circumference of the rotor and the shank part of the rotor generated by the force applied on the tip end of the rotary tool "A" during rotary cutting operation in case of FIG. 6b is smaller than that in case of FIG. 6a. Accordingly, abrasion caused by friction between the outer circumference of the shank part of the rotary tool and the inner circumference of the tool guide tube part is reduced in FIG. 6b and it hardly occurs that abrasion powder is accumulated and solidified between the shank part and the tool guide tube part and the rotary tool becomes non removable over time. When the force applied on the rotor at the base end side part "Z" from the circumscribed part is defined as F1a in FIG. 6a and as F2b in FIG. 6b, it can be expressed by the formulae F2a=F0L/L1, F2b=F0L/L2. Therefore, F2b becomes smaller than F2a and the force applied on the base end side part "Z" in FIG. 6b is smaller than that in FIG. 6a and it is understood that adverse effect of the chucking pawl on the elastic locking function at the base end part of the rotary tool is reduced.

The rotary tool is designed to be able to be inserted into or removed from the rotor, so that the inner diameter of the rotor is designed to be slightly larger than the outer diameter of the rotary tool. Therefore, it is inevitable the axial center of the rotor and the axial center of the rotary tool cause runout. Runout S2 of the axial center C0 of the rotary tool C and the axial center B0 of the rotor B in FIG. 6b is smaller than runout S1 of the axial center C0 of the rotary tool C and the axial center A0 of the rotor A in FIG. 6a and abrasion caused by friction of the rotary tool and the rotor when runout occurs is reduced.

FIG. 7 to FIG. 13 show a chuck mechanism in another embodiment and a dental handpiece incorporating the chuck mechanism. The chuck mechanism 1A is different from the chuck mechanism 1 in the above-mentioned embodiment in that a working body 13 which is formed in the shape of a cap and is movable in the axial direction is attached to cover a portion of the rotor outer member 5 where the rotary tool 2 is engaged so as not to be mutually rotatable in such a manner that the working body 13 is not disengageable or mutually rotatable. Although the structure of the rotor outer member 5 becomes slightly different because such a working body 13 is newly adopted, the structures of the rotor 3 and the chucking member 4 constituting the chuck mechanism 1A are the same as those of the rotor 3 and the chucking member 4 constituting the chuck mechanism 1 of the above-mentioned embodiment. Therefore, the members in common with the rotor 3, the chucking member 4, and the rotor outer member 5 in the above-mentioned embodiment have the same reference numerals. The chuck mechanism 1A in this embodiment has structure members based on the operation principle by the difference of the circumscribed length of the rotor to the rotary tool as explained in FIG. 6.

Figure 9:
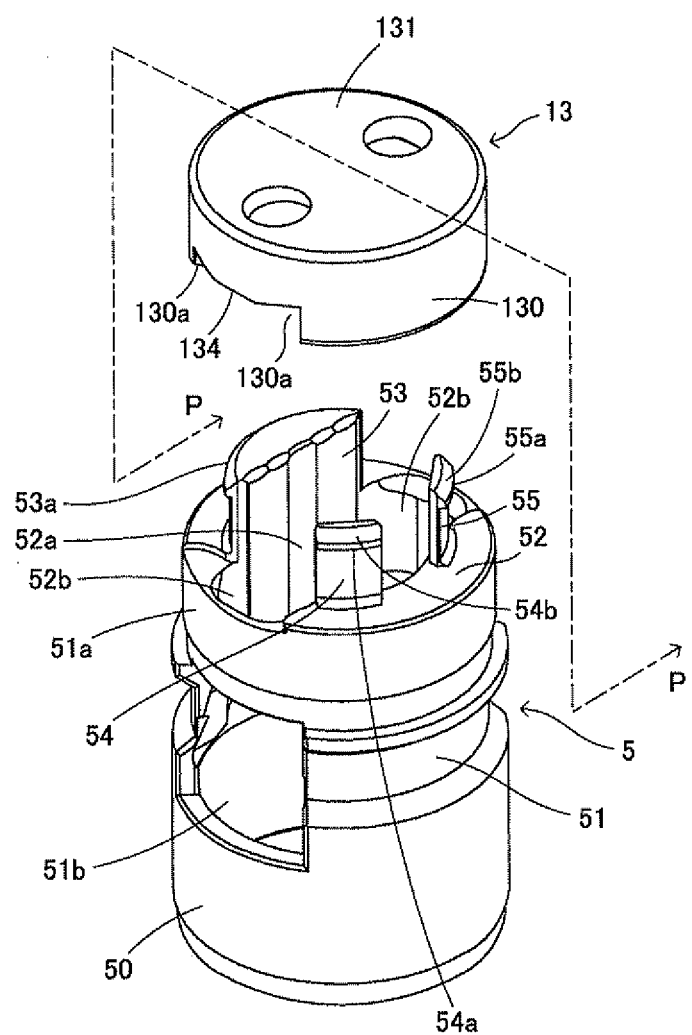
FIG. 9 is a broken perspective view showing the relation of the rotor outer member and the working body in the chuck mechanism in the embodiment.
Figure 11:
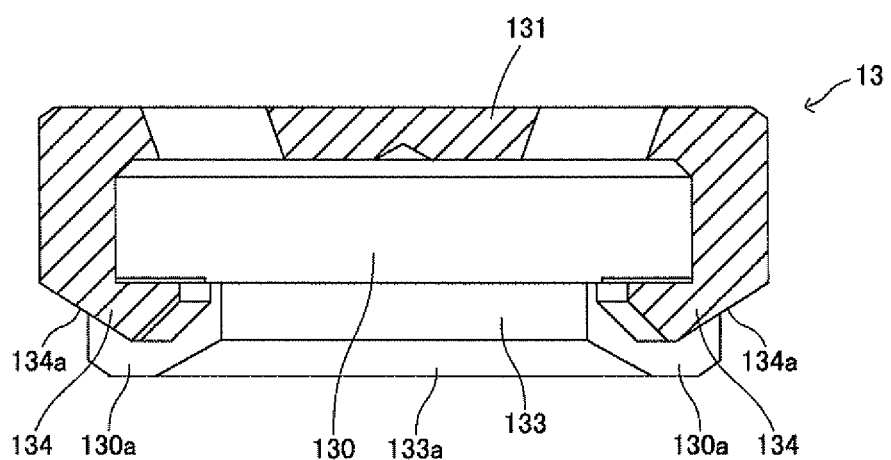
FIG. 11 is a sectional view taken along the arrow Q-Q in FIG. 10.

The structures of the rotor outer member 5 and the working body 13 of the chuck mechanism 1A in this embodiment are explained referring to FIG. 9 to FIG. 11. Three locking pieces 53, 54, 55 are provided for the disc part 52 of the rotor outer member 5 in a protruding manner in the axial direction so as to surround the receiving part 52a. The locking piece 53 is provided at a position corresponding to the ID-cut part 20b of the rotary tool 2 when the rotary tool 2 is inserted as to be mentioned later, and other locking pieces 54, 55 are provided symmetrically with respect to a center line of the locking piece 53 (corresponding to the line P-P) at a position corresponding to a curved surface other than the D-cut part 20b. The locking piece 53 is formed thick and the other locking pieces 54, 55 are formed thin so as to be elastically deformable. Locking chuck pawls 53a, 54a, 55a are formed at the projecting end of the locking pieces 53, 54, 55 in the centrifugal direction, respectively. The locking chuck pawls 53a, 54a, 55a are formed in the shape of a claw and have slant guide surfaces 53b, 54b, 55b on the outer circumference, respectively. Thin locking pieces 54, 55 are provided in addition to the thick locking piece 53 in the figures; however, only one thin locking piece may be provided opposite to the locking piece 53.

The working body 13 has a short cylindrical part 130 and a flat canopy part 131 closing one end of the cylindrical part 130. The other end of the cylindrical part 130 is provided with locking parts 132, 133 for attaching the working body 13 to the rotor outer member 5 movable in the axial direction and non-disengageable, and is further provided with a pair of operation parts 134, 134 (also refer to FIG. 12 and FIG. 13). The pair of operation parts 134, 134 are formed so as to face in the radial direction and the locking parts 132, 133 face each other so as to sandwich the operation parts 134, 134 via slit parts 130a . . . . The lower ends of the operation parts 134, 134 (the ends opposite to the canopy part 131) have cam surfaces 134a, 134a slant towards the upward centrifugal direction and the cam surfaces 134a, 134a are designed to face the cam-follower surfaces 42a, 42a of the chucking member 42 when the chuck mechanism 1A is assembled to be mentioned later. The locking parts 132, 133 are in the form of a claw so as to be engaged with the locking chuck pawls 53a, 54a, 55a of the rotor outer member 5 and have slant guide surfaces 132a, 133a which interfere with the guide surfaces 53b, 54b, 55b of the locking chuck pawls 53a, 54a, 55a.

The working body 13 constructed as mentioned above is attached to the rotor outer member 5 movable in the axial direction and non-disengageable. Namely, the working body 13 is positioned in such a manner that the lower end (opposite to the canopy part 131) of the working body 13 faces the disc part 52 of the rotor outer member 5, the pair of operation bodies 134, 134 face the pocket parts 52b, 52b, the locking part 132 faces the locking piece 53, and the locking part 133 faces the locking pieces 54, 55, respectively. Then, the working body 13 is pushed into the rotor outer member 5 in such a manner that the guide surface 132a of the locking part 132 is assigned to the guide surface 53b of the locking chuck pawl 53a, and the guide surface 133a of the locking part 133 is assigned to the guide surfaces 54b, 55b of the locking chuck pawls 54a, 55a, respectively. In this case, cam function of the guide surface 133a of the locking part 133 to the guide surfaces 54b, 55b of the locking chuck pawls 54a, 55a makes the locking pieces 54, 55 deformed in the centripetal direction. And pushing operation is further continued, the locking pieces 53, 54, 55 climb over the locking parts 132, 133 and fit into the cylindrical part 130 of the working body 13. Then, the locking parts 132, 133 of the working body 13 are locked by the locking pieces 53, 54, 55 by the elastic restoration operation of the locking pieces 54, 55 as shown with two-dotted lines in FIG. 10. Such a locked state is mutually fixed locking of claw-like parts, so that the working body 13 is attached to the rotor outer member 5 so as not to be disengageable and is also movable in the axial direction along the depth of the rotor outer member 5. The operation parts 134, 134 are formed so as to project in the centripetal direction from the inner wall of the cylindrical part 130. When the working body 13 is attached to the rotor outer member 5, the operation parts 134, 134 are interfered by the locking pieces 53, 54, 55 along the circumferential direction, so that the working body 13 cannot axially rotate relative to the rotor outer member 5 each other.

In actual assemble procedures of the chucking member 1A, the working body 13 is attached to the rotor outer member 5 as mentioned above after the rotor 3, the chucking member 4 and the rotor outer member 5 are assembled each other. The assembly procedures of the chuck mechanism 1A are explained referring to FIG. 7. Structure members other than the rotor outer member 5 and the working body 13 are the same as those shown in FIG. 1 and FIG. 2, so the same reference numerals are allotted to the common members and explanation of the same members is omitted. The cutout 30d provided for the rotor 3 in the above-mentioned embodiment does not exist in this embodiment; however, such an embodiment with the cutout is not excluded here. The assembly procedures in FIG. 7a to FIG. 7c are the same as those in FIG. 2a to FIG. 2c, so the explanation is also omitted here.

As shown in FIG. 7d, while the rotor 3, the chucking member 4 and the rotor outer member 5 are assembled each other, the working body 13 is attached to the rotor outer member 5 so as to cover the disc part 52 as mentioned above. In such a state, the cam surfaces 134a, 134a of the working body 13 are positioned so as to face the cam-follower surfaces 42a, 42a of the chucking member 4 (also refer to FIG. 12). Thereby, assembly of the chuck mechanism 1A in this embodiment is completed. Then, as shown in FIG. 7e, the base end side bearing 6 and the tip side bearing 7 are fitted to the tubular bearing holding part 51a of the rotor outer member 5 and to the outer circumference 30c on the tip side of the rotor 3, respectively. The assembled chuck mechanism 1A is incorporated to a predetermined portion of the head part 9 of the dental handpiece 8A shown in FIG. 12 and FIG. 13.

FIG. 8a and FIG. 8b show assembly procedures of the rotary tool 2 to the chuck mechanism 1A assembled to the head part 9. In FIG. 8, the head part 9 is not shown for convenience as in FIG. 3. The assembly procedures of the rotary tool 2 are the same as those explained referring to FIG. 3a and FIG. 3b, so its explanation is omitted here. The base end part 20 including the D-cut part 20b of the rotary tool 2 which is engaged with the rotor outer member 5 in a mutually non-rotatable manner is covered by the working body 13.

Figure 12:
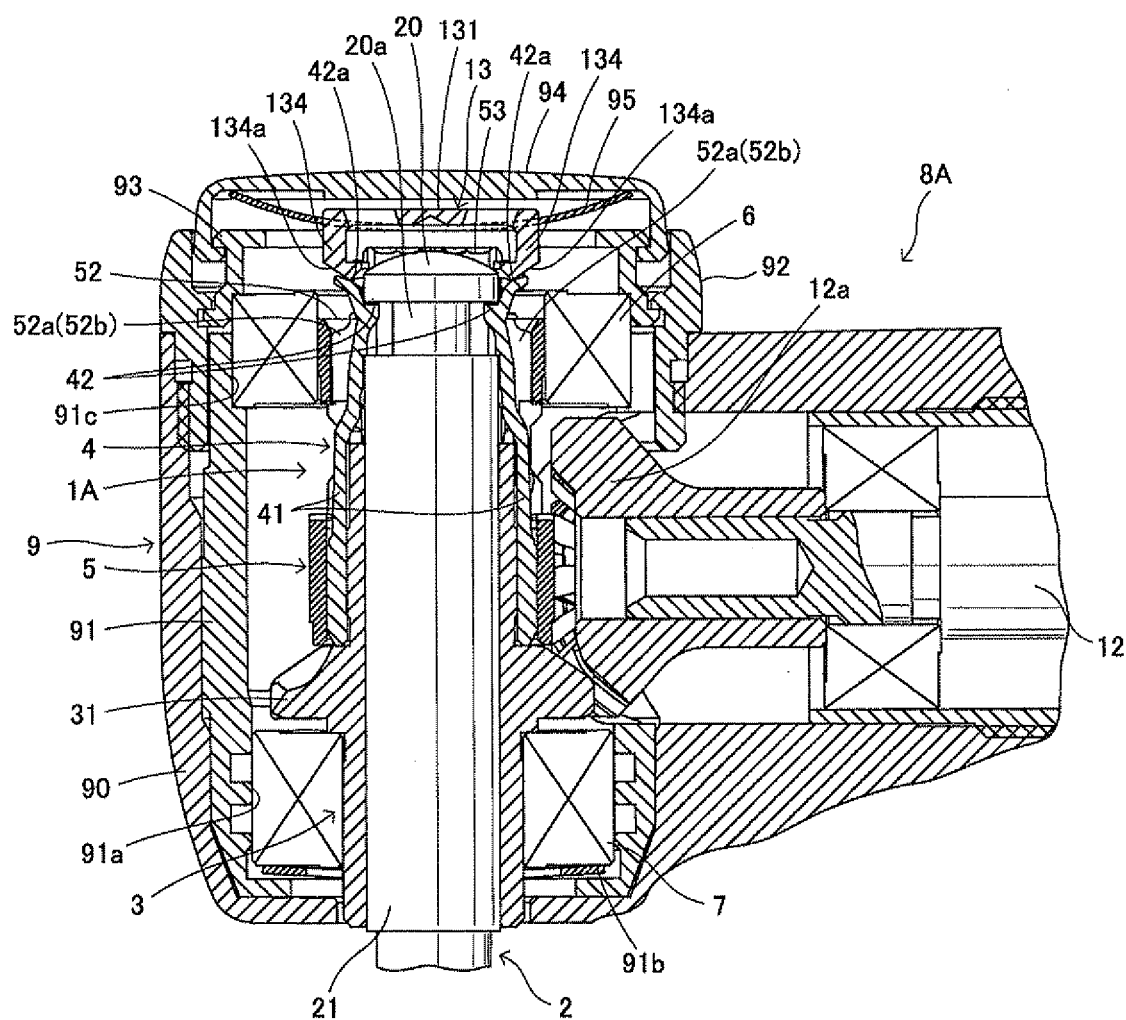
FIG. 12 is a partially broken sectional view of an essential part of the dental handpiece having the chuck mechanism in the embodiment.
Figure 13:
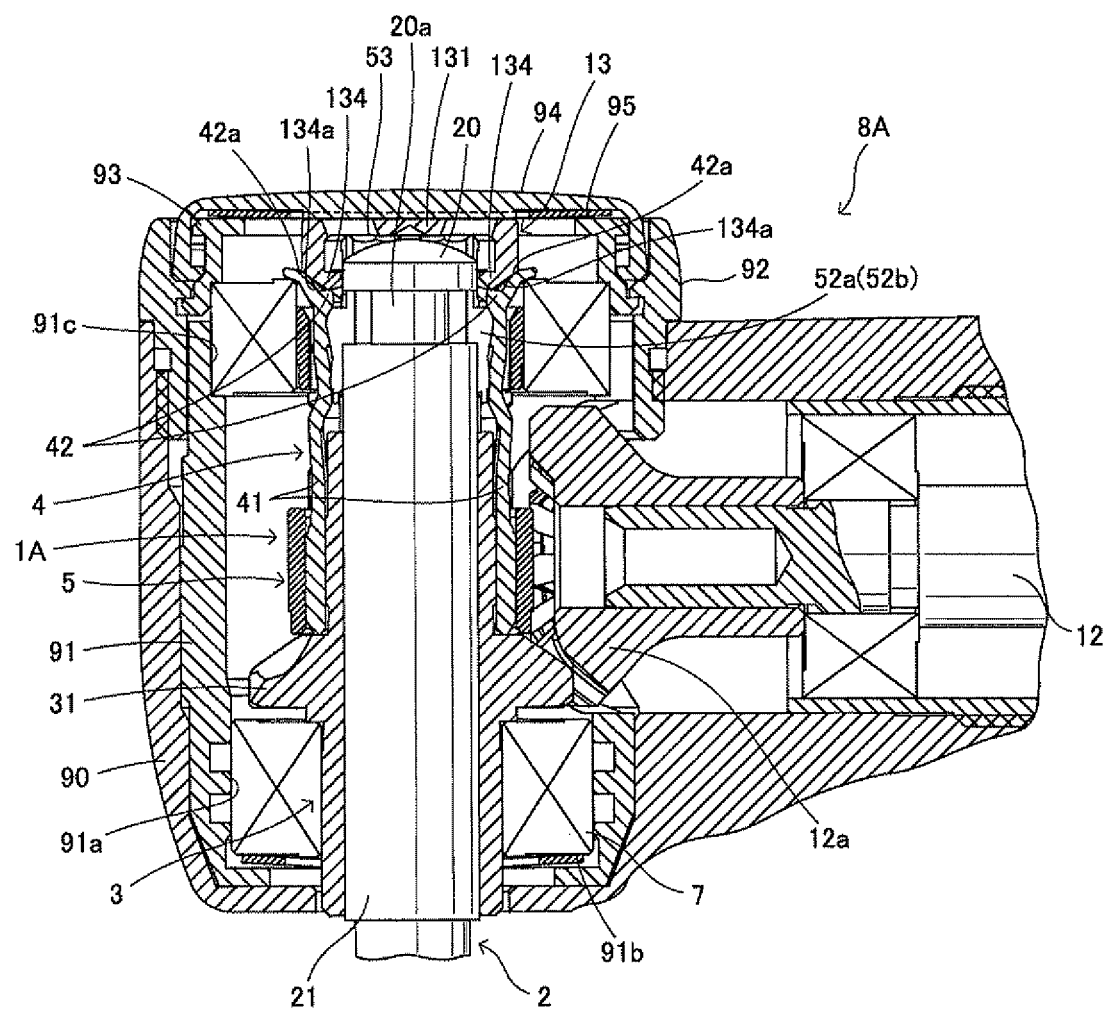
FIG. 13 is a similar view to FIG. 12 showing removing procedures of the rotary tool from the dental handpiece having the chuck mechanism in the embodiment.
Figure 14A:
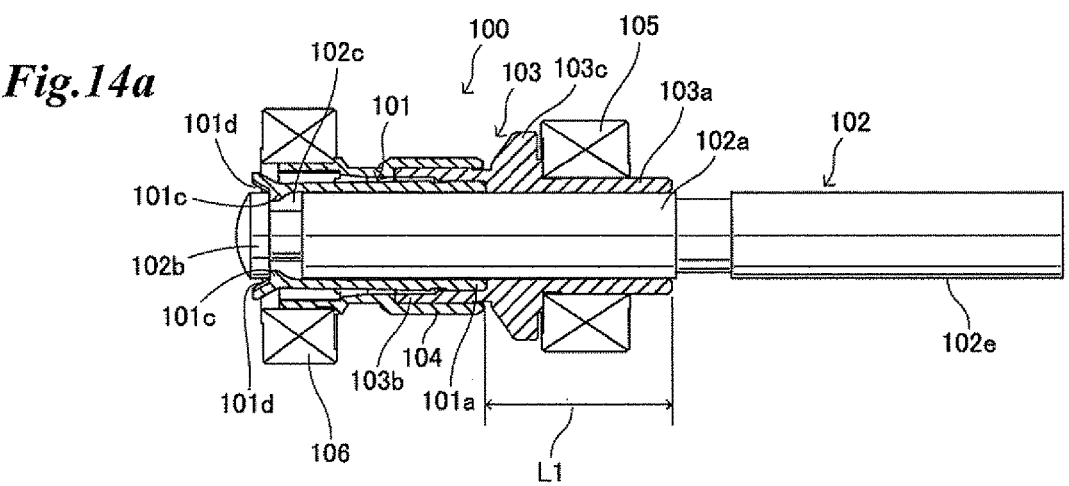
FIG. 14a, FIG. 14b, and FIG. 14c show one embodiment of a conventional chuck mechanism.
Figure 14B:
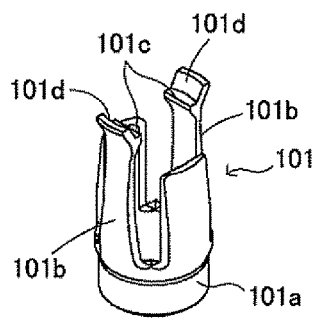
Figure 14C:
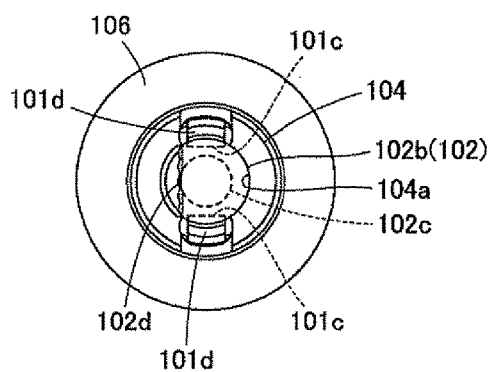

FIG. 12 and FIG. 13 show one embodiment of a dental handpiece incorporating the chuck mechanism 1A. The basic structure of the dental handpiece 8A shown in the figures is the same as that of the dental handpiece 8 shown in FIG. 4 and FIG. 5; however, the structure of the push button 94 is different according to the structure of the chuck mechanism 1A. Therefore, the same reference numerals are allotted to the common members other than the push button 94 and the chuck mechanism 1A and their explanation is omitted here.

The lower surface of the push button 94 in this embodiment is formed flat facing the canopy part 131 of the working body 13 without having the cylindrical projection 94a as in the above-mentioned embodiment. According to the structure of this embodiment, if the push button 94 is not pressed, the lower surface of the push button 94 and the canopy part 131 are in a non-contact state. If the push button 94 is pressed against the elastic force of the disc spring 95, the lower surface of the push button 94 comes to abut the upper surface of the canopy part 131 and the working body 13 is pushed down. When the push button is pressed against the elastic force of the disc spring 95 relative to the chuck mechanism 1A incorporated in the head part 9, the working body 13 is pushed down, the cam surfaces 134a, 134a of the operation parts 134, 134 of the working body 13 operate on the cam-follower surfaces 42a, 42a of the chucking member 4. Then, the elastic chucking pieces 41, 41 are elastically reamed in the centrifugal direction and the chucking pawls 42, 42 of the chucking member 4 are displaced each other in opposite direction (centrifugal direction). Therefore, the push button 94 and the disc spring 95 constitute a chuck release means of the rotary tool also in this embodiment. In the above-mentioned state, based on the procedures shown in FIG. 8a and FIG. 8b, the rotary tool 2 is inserted to the tool guide tube part 30 facing the lower end of the head part 9 and is kept in an axially rotatable manner in the head part 9 together with the rotor 3, the chucking member 4 and the rotor outer member 5. The dental handpiece 8A can be used for cutting treatment for teeth as mentioned above.

FIG. 13 shows procedures of chuck release of the rotary tool 2 from the chuck mechanism 1A, namely removal of the rotary tool 2 from the rotor 3. When the push button 94 is pressed in the axial center direction of the rotary tool 2 against the elastic force of the disc spring 95 while the rotor 3 stops rotating, the lower surface of the push button 94 abuts the upper surface of the canopy part 131 of the working body 13 and the working body 13 is pushed down. Then, the cam surfaces 134a, 134a of the operation parts 134, 134 operate on the cam-follower surfaces 42a, 42a of the chucking member 4, the elastic chucking pieces 41, 41 are elastically deformed in the centrifugal direction, and the chucking pawls 42, 42 of the chucking member 4 are displaced in separated direction each other and are disengaged from the locking groove 20a. The cutting operation part 22 is pulled out with finger 22 in such a state, and the rotary tool 2 can be removed from the rotor 3.

According to such a dental handpiece, the rotary speed of the rotary tool 2 is set at about 40,000 rpm and the rotary tool 2 is frequently exchanged depending on treatment. Some operators turn off the rotor 3 and press the push button 94 while the rotary tool 2 still rotates through inertia. According to the dental handpiece 8 in the above-mentioned embodiment, the cam surfaces 94b, 94b of the push button 94 come to abut the cam-follower surfaces 42a, 42a which still rotate through inertia at high speed just when rotation stops, thereby proceeding abrasion of the abutting surfaces of them. When such abrasion of the surfaces having cam function proceeds, chuck release function is deteriorated over time and the rotor 2 sometimes becomes unable to be removed rapidly from the rotor 3. However, according to the dental handpiece 8A of this embodiment, the working body 13 is designed to be integrally rotated with the rotor 3, so that even when the push button 94 is pressed while the rotor 3 rotates through inertia, the cam surfaces 134a, 134a of the working body 13 and the cam-follower surfaces 42a, 42a are in an abutted state in which abrasion by the mutual rotation does not occur. Therefore, there is no fear that the chuck release function is deteriorated over time when abrasion of the surfaces having cam function proceeds and the rotary tool 2 cannot be easily removed from the rotor 3.

According to the hand-held piece disclosed in PTL2, abrasion resistance is reduced by interposing a ball between the manual button constituting the chuck release means and the pusher and the above-mentioned abrasion is reduced. However, the chuck mechanism is different from that of the present invention. According to the dental handpiece 8, 8A of the present invention, when the rotary tool 2 is attached to the chuck mechanism 1, 1A incorporated in the head part 9, the push button 94 is pressed, the cam-follower surfaces 42a, 42a are made apart in the centrifugal direction, and the base end part 20 including the D-cut part 20b of the rotary tool 2 is inserted and engaged with the receiving part 52a by fumbling while manipulating the rotary tool 2 in the axial direction. When the rotor 3 is in a freely rotatable manner or substantially in such a manner, the rotor 3 is rotated together when the rotary tool 2 is manually rotated, and the above-mentioned inserting and engaging operation cannot be easily executed. Although the abrasion resistance can be reduced by the ball in PTL 2, there is a fear that the rotor 3 is rotated together and the rotary tool 2 cannot be easily inserted and engaged when such a ball is used in the chuck mechanism of the present invention. On the other hand, according to the dental handpiece 8A of this embodiment, the lower surface of the push button 94 and the upper surface of the canopy 131 of the working body 13 are in surface contact, so that braking force increases and the rotor 3 does not rotate together with manipulation of the rotary tool 2, thereby rapidly inserting and engaging the rotary tool 2.

The dental handpiece 8A of this embodiment has high degree of usefulness in which noticeable abrasion preventing function of the surface having cam function and smooth function of insertion and locking of the rotary tool are both provided in addition to the common function to the dental handpiece 8 of the above-mentioned embodiment.

In the above-mentioned embodiment, a preferable embodiment has a pair of axisymmetrically elastic chucking pieces 41 of the chucking member 4; however, the present invention is not limited to such an embodiment and one or more than three elastic chucking pieces can be provided. A micro-motor hand-held piece is exemplified as a dental handpiece to which the chuck mechanism of the present invention is applied; however, an air turbine hand-held piece or a hand-held piece to which another rotary tool is detachably attached can be used. In addition, the shape of the rotary tool is not limited to those shown in the figures.

The invention claimed is:

1. A chuck mechanism in combination with a columnar rotary tool for use in a dental handpiece, the chuck mechanism holding the columnar rotary tool, the combination comprising:
   the columnar rotary tool having a shank part and a locking groove, the shank part having a base end side and a tip side, the locking groove positioned nearer the base end side of the shank part than the tip side; and
   the chuck mechanism having an annular rotor, and an annular chucking member mounted to the annular rotor, the annular chucking member including
      a cylindrical base part that fits with and surrounds the annular rotor; and
      a plurality of chucking pieces, each chucking piece including
         an abutting part extending in an axial direction from the cylindrical base part, the abutting part being elastically deformable in a radial direction such that a radially inner main surface of the abutting part elastically abuts against a portion of an outer circumference of the shank part in the radial direction, the portion of the outer circumference of the shank part being positioned between the locking groove and the tip side of the shank part, and
         a chucking pawl projecting radially inward from a tip end of the abutting part such that the chucking pawl elastically engages the locking groove of the columnar rotary tool,
      wherein the radially inner main surface of the abutting part faces in a direction that is perpendicular to a center axis of the columnar rotary tool.

2. The chuck mechanism in combination with the columnar rotary tool according to claim 1, the chuck mechanism further comprising a pair of chucking pieces diametrically opposing each other.

3. The chuck mechanism in combination with the columnar rotary tool according to claim 1, the chuck mechanism further comprising a tubular rotor outer member fitted to an external area of the cylindrical base part of the annular chucking member,
   wherein the columnar rotary tool has a rotary tool base part that engages an inner surface of the tubular rotor outer member such that the columnar rotary tool and the tubular rotor outer member are not rotatable relative to each other.

4. The chuck mechanism in combination with the columnar rotary tool according to claim 3, the chuck mechanism further comprising a bearing attached on a radially outward part of the tubular rotor outer member,
   wherein the annular rotor is rotatably fitted to a head part of the dental handpiece via the bearing.

5. The chuck mechanism in combination with the columnar rotary tool according to claim 4, wherein the bearing is fitted to a corresponding region where the chucking pawl and the locking groove are engaged.

6. The chuck mechanism in combination with the columnar rotary tool according to claim 3, the chuck mechanism further comprising:
a working body movable along an axis of the tubular rotor outer member,
wherein the working body and the tubular rotor outer member are not rotatable relative to each other, and
wherein the working body has an operation part for deforming one of the plurality of chucking pieces via movement of the working body.

7. The chuck mechanism in combination with the columnar rotary tool according to claim 6, wherein the working body has a short cylindrical part and a flat canopy part for covering one end of the short cylindrical part, and
wherein the short cylindrical part is provided with the operation part and a locking part for attaching the working body to the tubular rotor outer member movably in an axial direction of the axis of the tubular rotor outer member.

8. A dental handpiece, comprising:
the chuck mechanism in combination with the columnar rotary tool of claim 1, wherein the chuck mechanism is provided at a head part;
a hand-held piece body;
the head part connected to a front end of the hand-held piece body;
a rotary drive portion built in the hand-held piece body;
a rotation transmitting portion for transmitting rotary force from the rotary drive portion to the columnar rotary tool; and
a manual button for releasing the chuck mechanism,
wherein the columnar rotary tool is held via the chuck mechanism and is constructed such that it rotates together with the annular rotor about an axis by rotary force transmitted from the rotation transmitting portion.

9. A chuck mechanism in combination with a columnar rotary tool for use in a dental handpiece, the chuck mechanism holding the columnar rotary tool, the combination comprising:
the columnar rotary tool having a shank part and a locking groove, the shank part having a base end side and a tip side, the locking groove positioned nearer the base end side of the shank part than the tip side; and
the chuck mechanism having an annular rotor, and an annular chucking member mounted to the annular rotor, the annular chucking member including
a cylindrical base part that fits with and surrounds the annular rotor; and
a plurality of chucking pieces, each chucking piece including
an abutting part extending in an axial direction from the cylindrical base part, the abutting part being elastically deformable in a radial direction such that a radially inner main surface of the abutting part elastically abuts against a portion of an outer circumference of the shank part in the radial direction, the portion of the outer circumference of the shank part being positioned between the locking groove and the tip side of the shank part, and
a chucking pawl projecting radially inward from a tip end of the abutting part such that the chucking pawl elastically engages the locking groove of the columnar rotary tool,
wherein the radially inner main surface of the abutting part is located between the chucking pawl and the cylindrical base part, and
wherein the radially inner main surface of the abutting part faces in a direction that is perpendicular to a center axis of the columnar rotary tool.

* * * * *